US010426965B2

(12) United States Patent
Bowers (10) Patent No.: US 10,426,965 B2
(45) Date of Patent: Oct. 1, 2019

(54) METHOD AND APPARATUS FOR DETERMINING BATTERY CAPACITY IN A DEFIBRILLATOR

(71) Applicant: Scion Medical Limited, Mong Kok (HK)

(72) Inventor: Kyle R. Bowers, Boxborough, MA (US)

(73) Assignee: Scion Medical Limited, Hong Kong (HK)

( * ) Notice: Subject to any disclaimer, the term of this patent is extended or adjusted under 35 U.S.C. 154(b) by 0 days.

(21) Appl. No.: 15/213,047

(22) Filed: Jul. 18, 2016

(65) Prior Publication Data

US 2017/0043176 A1    Feb. 16, 2017

Related U.S. Application Data

(63) Continuation of application No. 12/806,053, filed on Aug. 4, 2010, now abandoned, which is a
(Continued)

(51) Int. Cl.
*A61N 1/39*    (2006.01)
*G01R 31/367*    (2019.01)
(Continued)

(52) U.S. Cl.
CPC ......... *A61N 1/3975* (2013.01); *A61N 1/3925* (2013.01); *A61N 1/3993* (2013.01);
(Continued)

(58) Field of Classification Search
CPC ........................... H02J 7/0047; H02J 2007/005
(Continued)

(56) References Cited

U.S. PATENT DOCUMENTS 4,677,363 A    6/1987    Kopmann
4,945,477 A    7/1990    Edwards
(Continued)

FOREIGN PATENT DOCUMENTS

EP    1072285    1/2001
EP    1250944    10/2002
(Continued)

OTHER PUBLICATIONS

Elaine Fitzgibbon et al., "Determination of the noise source in the electrocardiogram during cardiopulmonary resuscitation", Critical Care Medicine, 2002, S148-S153, vol. 30, No. 4.
(Continued)

*Primary Examiner* — Alyssa M Alter
(74) *Attorney, Agent, or Firm* — Pandiscio & Pandiscio (57) ABSTRACT

A defibrillator system and associated methodology for determining capacity of a battery and/or a number of battery cells contained in a pack. The system measures and stores the battery or battery pack voltage signal data and uses an algorithm to determine the remaining capacity. The algorithm takes into account the operating mode of the device, historical information of the device including, but not limited to, how long it has been since the device has been used, how the device has been used (e.g. shocking mode or idle mode), how many times the device has been used with its installed battery or battery pack, how many charging cycles and/or shocks have been delivered etc. The output from the system is fed back to the user to inform the user when the battery is low, needs to be replaced and/or how many remaining shocks are left the battery.

2 Claims, 9 Drawing Sheets

Related U.S. Application Data continuation of application No. 11/193,940, filed on Jul. 29, 2005, now abandoned.

(60) Provisional application No. 60/592,788, filed on Jul. 30, 2004.

(51) Int. Cl.
    *G01R 31/36*     (2019.01)
    *H02J 7/00*     (2006.01)
    *H02J 7/34*     (2006.01)

(52) U.S. Cl.
    CPC ....... *G01R 31/367* (2019.01); *G01R 31/3646* (2019.01); *H02J 7/0047* (2013.01); *H02J 7/0054* (2013.01); *H02J 7/345* (2013.01); *H02J 2007/005* (2013.01); *H02J 2007/0096* (2013.01)

(58) Field of Classification Search
    USPC .......................................................... 607/5
    See application file for complete search history.

(56) References Cited

U.S. PATENT DOCUMENTS

| | | |
|---|---|---|
| 5,302,907 A | 4/1994 | Hohenstein et al. |
| 5,741,307 A | 4/1998 | Kroll |
| 5,999,852 A | 12/1999 | Elabbady et al. |
| 6,035,235 A | 3/2000 | Perttu et al. |
| 6,108,579 A | 8/2000 | Snell et al. |
| 6,125,299 A | 9/2000 | Groenke et al. |
| 6,247,474 B1 | 6/2001 | Greeninger et al. |
| 6,287,328 B1 | 9/2001 | Snyder et al. |
| 6,304,773 B1 | 10/2001 | Taylor et al. |
| 6,304,779 B1 | 10/2001 | Yerkovich |
| 6,313,609 B1 | 11/2001 | Brink |
| 6,351,671 B1 | 2/2002 | Myklebust et al. |
| 6,366,809 B1 * | 4/2002 | Olson .................. A61N 1/3975 607/29 |
| 6,693,431 B1 | 2/2004 | Leyde et al. |
| 6,820,019 B1 | 11/2004 | Kelly et al. |
| 2002/0099416 A1 | 7/2002 | Dooley et al. |

FOREIGN PATENT DOCUMENTS

| | | |
|---|---|---|
| WO | WO 97/22014 | 6/1997 |
| WO | WO 98/39060 | 9/1998 |

OTHER PUBLICATIONS

John Hakon Husoy et al., "Removal of Cardiopulmonary Resuscitation Artifacts From Human ECG Using an Efficient Matching Pursuit-Like Algorithm", IEEE Transactions on Biomedical Engineering, Nov. 2002, 1287-1298, vol. 49, No. 11.

Anouk P. Van Alem et al., "Interruption of Cardiopulmonary Resuscitation With the Use of the Automated External Defibrillator in Out-of-Hospital Cardiac Arrest", Annals of Emergency Medicine, Jul. 2003, 1-9, 42:X.

Ting Yu et al., "Adverse Outcomes of Interrupted Precordial Compression During Automated Defibrillation", Circulation, Jul. 16, 2002, 368-372.

* cited by examiner

METHOD AND APPARATUS FOR DETERMINING BATTERY CAPACITY IN A DEFIBRILLATOR

REFERENCE TO PENDING PRIOR PATENT APPLICATIONS

This patent application is a continuation of pending prior U.S. patent application Ser. No. 12/806,053, filed Aug. 4, 2010 by Kyle R. Bowers for METHOD AND APPARATUS FOR DETERMINING BATTERY CAPACITY IN A DEFIBRILLATOR, which in turn is a continuation of prior U.S. patent application Ser. No. 11/193,940, filed Jul. 29, 2005 by Kyle R. Bowers for METHOD AND APPARATUS FOR DETERMINING BATTERY CAPACITY IN A DEFIBRILLATOR, which in turn claims benefit of prior U.S. Provisional Patent Application Ser. No. 60/592,788, filed Jul. 30, 2004 by Kyle R. Bowers for METHOD AND SYSTEM FOR DETERMINING DEFIBRILLATOR BATTERY CAPACITY.

The above-identified patent applications are hereby incorporated herein by reference

FIELD OF THE INVENTION

The present invention relates generally to the measurement of battery capacity. More particularly, the present invention relates to the measurement and determination of the remaining capacity of a battery or battery pack in a defibrillator system.

BACKGROUND OF THE INVENTION

Approximately 350,000 deaths occur each year in the United States, due to sudden cardiac arrest (SCA). Many of these deaths can be prevented if effective defibrillation is administered within 3-5 minutes of SCA.

Sudden cardiac arrest is the onset of an abnormal heart rhythm, lack of pulse and absence of breath, leading to a loss of consciousness. If a pulse is not restored within a few minutes, death occurs. Most often, SCA is due to ventricular fibrillation, a chaotic heart rhythm that causes an uncoordinated quivering of the heart muscle. The lack of coordinated heart muscle contractions results in insufficient blood flow to the brain and other organs. Unless this chaotic rhythm is terminated, allowing the heart to restore its own normal rhythm and thus normal blood flow to the brain and other organs, death ensues.

Rapid defibrillation is the only known means to restore the normal heart rhythm and prevent death after SCA due to ventricular fibrillation. For each minute that passes after the onset of SCA, the mortality rate increases by 10%. If defibrillated within 1-2 minutes, a patient's survival rate can be as high as 90% or more. At 7-10 minutes, the patient's survival rate drops below 10%. Therefore, the only way to increase the survival chances for an SCA victim is through early defibrillation.

Automatic External Defibrillators (AEDs) can provide early access to defibrillation, but they must be portable so they can be easily carried to a victim of SCA, easy-to-use so that they can be properly utilized when SCA occurs, and easily maintained. In addition, AEDs must be inexpensive, so that they can be broadly deployed.

Additionally, AEDs require a portable energy source to enable the device to be deployed quickly to treat a victim of SCA. Often, the victim may be in a remote or difficult-to-reach area, making compact and portable AEDs attractive to police, EMT, Search-And-Rescue and other rescue or emergency services.

AEDs must remain in a standby mode for extended periods of time. Most current AEDs are rated for two years of standby and must be able to complete a sufficient number of shocks at the end of this period. However, during this two-year standby period, the battery pack may discharge significantly and thus may not have sufficient capacity to provide therapy, especially in situations which may require many defibrillation shocks and an extended period of monitoring time.

Currently, many AEDs use a battery monitoring circuit, also known as a "smart battery", to provide a "fuel gauge" for remaining capacity. This technique requires the use of low power analog and digital circuitry within the battery pack or the device to constantly monitor battery capacity. Most of these devices also monitor battery temperature in order to accurately gauge capacity. As those skilled in the art can appreciate, the disadvantage of this technique is that the additional circuitry, components and connections needed to monitor battery capacity may add significant cost to the battery pack and/or the AED itself. As is well known to those skilled in the art, this technique has been historically problematic and has been an issue with portable AEDs that use either disposable or rechargeable battery packs.

SUMMARY OF THE INVENTION

The present invention addresses the deficiencies described above by providing a novel method and apparatus for determining the capacity of a battery and/or a number of battery cells contained in a battery pack.

In accordance with the present invention, the defibrillation system contains a battery or battery pack, a circuit to charge the defibrillation capacitor or capacitors, and a circuit to deliver a biphasic waveform.

In accordance with the present invention, the defibrillation system contains an LCD display and voice playback circuitry, an audio amplifier and a speaker to notify the user of events during device operation.

In accordance with the present invention, the defibrillation system contains a microprocessor and circuitry that measures the battery terminal or battery pack terminal voltage, digitizes the signal and stores the data in local memory for analysis.

In another aspect of the present invention, the defibrillation system stores the battery data in flash memory for post-incident analysis.

In another aspect of the present invention, the defibrillation system applies filtering techniques before and/or after storing the measured battery voltage signal data.

In another aspect of the invention, the defibrillation system uses an algorithm to determine the remaining capacity of the battery or battery pack.

In another aspect of the present invention, the defibrillation system stores in memory the measured battery terminal or battery pack terminal voltage and its associated operational mode. The different operating modes draw various levels of current from the battery or battery pack. The algorithm then uses this stored data to determine the remaining capacity of the battery or battery pack.

In another aspect of the present invention, the defibrillation system stores in memory how long the device has been used. The algorithm then uses this stored data to determine the remaining capacity of the battery or battery pack.

In another aspect of the present invention, the defibrillation system stores in memory the measured battery terminal or battery pack terminal voltage and how long the device has been used. The algorithm then uses this stored data to determine the remaining capacity of the battery or battery pack.

In another aspect of the present invention, the defibrillation system stores in memory the measured battery terminal or battery pack terminal voltage and how many times the device has been used with its installed battery or battery pack. The algorithm then uses this stored data to determine the remaining capacity of the battery or battery pack.

In another aspect of the present invention, the defibrillation system stores in memory the measured battery terminal or battery pack terminal voltage and how many times the device has been used to charge its internal capacitors with its installed battery or battery pack. The algorithm then uses this stored data to determine the remaining capacity of the battery or battery pack.

In another aspect of the present invention, the defibrillation system stores in memory how many times the device has been used to deliver a biphasic shock to a patient with its installed battery or battery pack. The algorithm then uses this stored data to determine the remaining capacity of the battery or battery pack.

In another aspect of the present invention, the defibrillation system stores in memory the measured battery terminal or battery pack terminal voltage and how many times the device has been used to deliver a biphasic shock to a patient with its installed battery or battery pack. The algorithm then uses this stored data to determine the remaining capacity of the battery or battery pack.

In another aspect the present invention, the algorithm uses the stored data to determine the remaining capacity of the battery or battery pack and informs the user audibly and/or visually that the battery or battery pack is low.

In another aspect the present invention, the algorithm uses the stored data to determine the remaining capacity of the battery or battery pack and informs the user that the battery or battery pack needs to be replaced.

In another aspect the present invention, the algorithm uses the data to determine the remaining capacity of the battery or battery pack and informs the user of the number of shocks left.

In another aspect the present invention, the algorithm uses the data to determine the remaining capacity of the battery or battery pack and informs the user of the remaining monitor time.

In another aspect the present invention, the algorithm uses the data to determine the remaining capacity of the battery or battery pack and informs the user of the general battery capacity as it relates to typical use, as for example, by displaying a "fuel gauge".

In one form of the invention, there is provided a method for determining the remaining battery capacity of a battery in a defibrillator, the method comprising:
applying an algorithm that calculates remaining battery capacity of a battery using measured battery voltage value in conjunction with historical information previously stored in the defibrillator.

In another form of the invention, there is provided a defibrillator comprising:
at least one battery;
at least one capacitor;
a circuit to charge the at least one capacitor from the at least one battery;
a circuit to deliver a biphasic waveform from the at least one capacitor to the patient;
user notification apparatus for notifying the user of events during defibrillator operation; and
a data acquisition circuit that measures the terminal voltage of the at least one battery, digitizes the signal and stores the data in memory for analysis.

In another form of the invention, there is provided a method for determining battery capacity in a defibrillator comprising:
recording historical data comprising at least one from the group consisting of:
how long it has been since the battery was last charged;
how the defibrillator has been used since the battery was last charged, including a record of when the defibrillator was in idle mode and when the defibrillator was in shocking mode;
how many shocks have been delivered since the battery was last recharged;
how long has it been since the defibrillator was last used in shocking mode; and
how many times the battery has been recharged over its lifetime;
measuring the current battery voltage; and
applying an algorithm to calculate remaining battery capacity, using the measured battery voltage and the recorded historical data.

In another form of the invention, there is provided apparatus for determining the battery capacity in a defibrillator comprising:
apparatus for recording historical data comprising at least one from the group consisting of:
how long it has been since the battery was last charged;
how the defibrillator has been used since the battery was last charged, including a record of when the defibrillator was in idle mode and when the defibrillator was in shocking mode;
how many shocks have been delivered since the battery was last recharged;
how long has it been since the defibrillator was last used in shocking mode; and
how many times the battery has been recharged over its lifetime;
apparatus for measuring the current battery voltage; and
apparatus for applying an algorithm to calculate remaining battery capacity, using the measured battery voltage and the recorded historical data.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENTS

The present invention discloses a system and method for determining the remaining capacity in the battery pack of a defibrillator.

Figure 1:
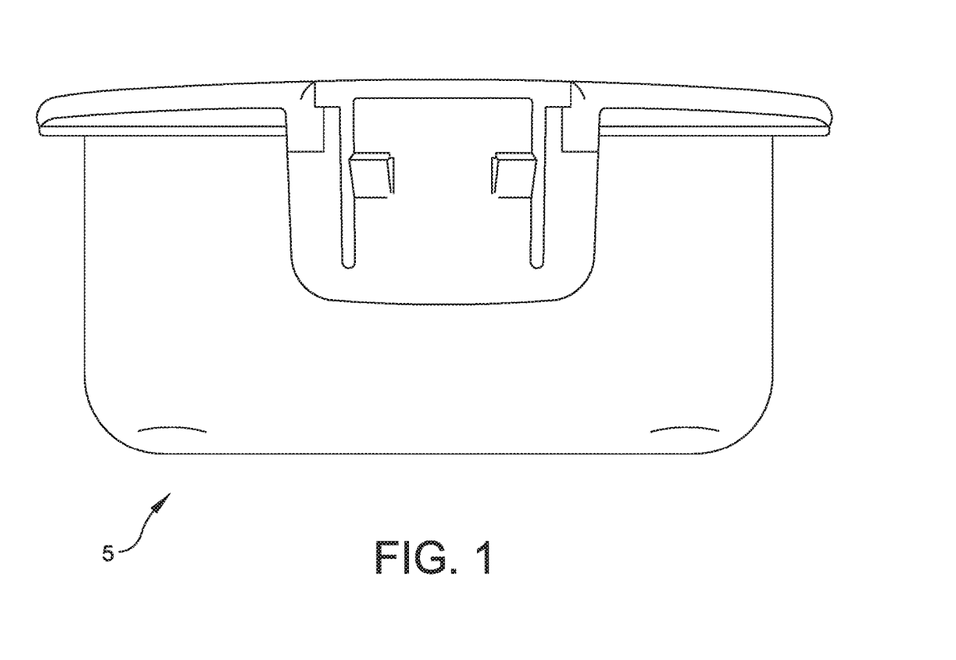
FIG. 1 is an illustration of a battery pack containing battery cells.
Figure 2:
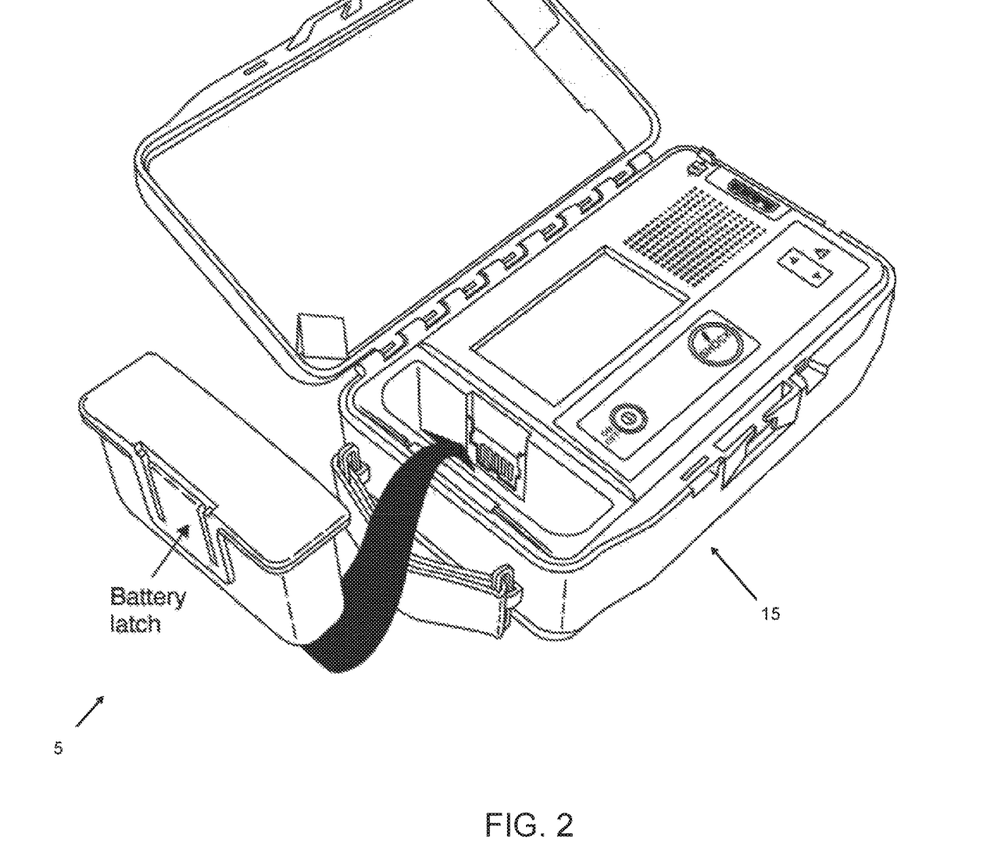
FIG. 2 shows how the battery pack is inserted into the defibrillator.

Looking first at FIGS. 1 and 2, there is shown the battery pack 5 of a defibrillator 15. It should be appreciated that the present invention may be applied the entire battery pack 15 or to individual cells of the battery pack.

In current defibrillator systems, it is difficult to determine the remaining capacity of the battery cells of a defibrillator. The battery pack voltage during idle mode (i.e., during the monitoring mode) yields little information about the remaining battery capacity due to the lack of cell load. In addition, as the batteries become depleted over time, the internal impedance of the cell increases. When the defibrillator begins charging the capacitors to deliver a shock, the battery load is significantly increased, thereby lowering the cell voltage. In cases where the battery is depleted, the battery cell impedance is high and the voltage may decrease to a level insufficient to charge the capacitors and provide defibrillation therapy.

Figure 5:
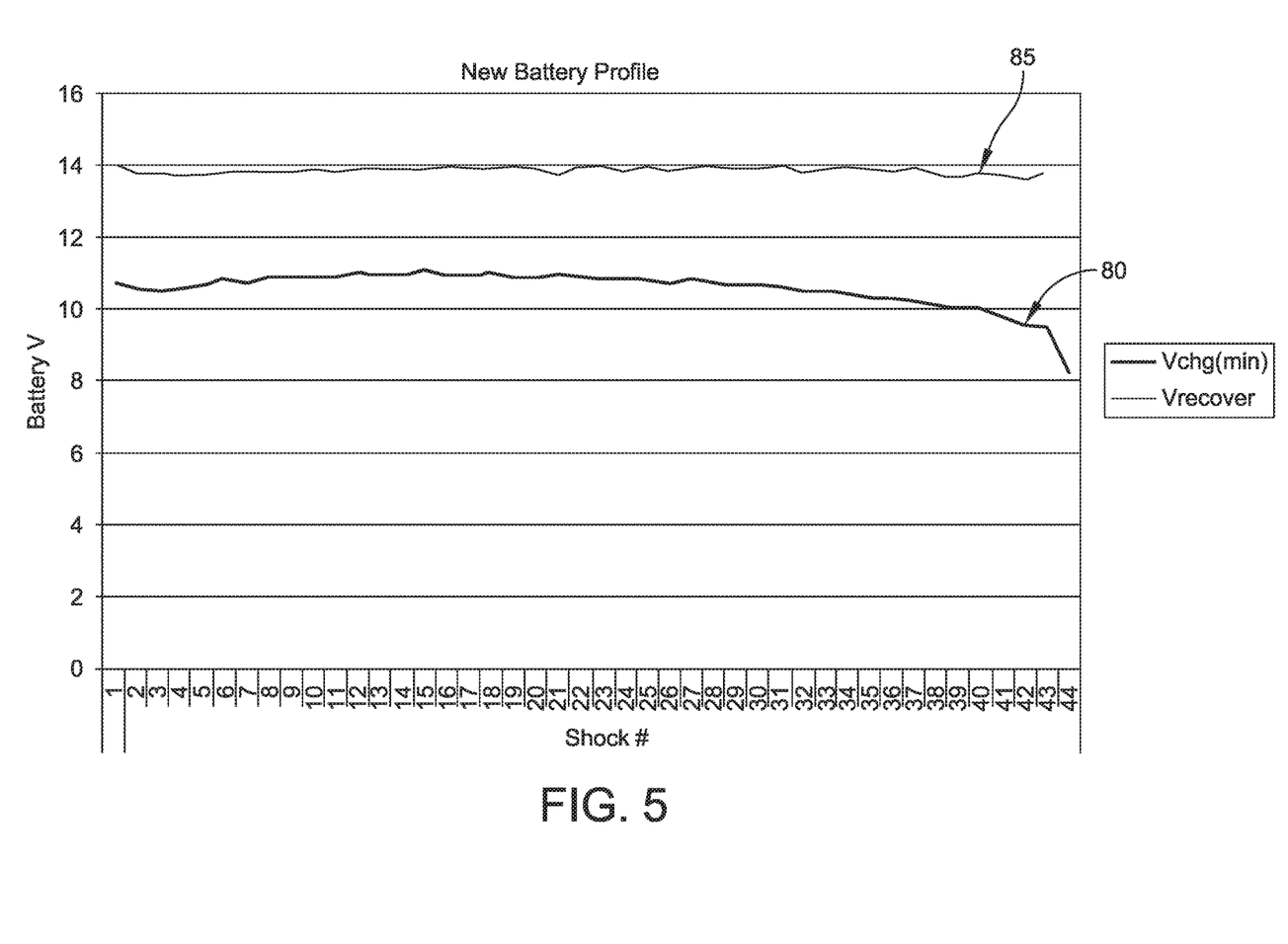
FIG. 5 is a profile of a new battery pack run in the defibrillator for a number of continuous shock cycles, wherein two voltages, i.e., the minimum voltage during charging (Vchg(min)) and the recovered voltage in between shocks (Vrecover), are measured.
Figure 6:
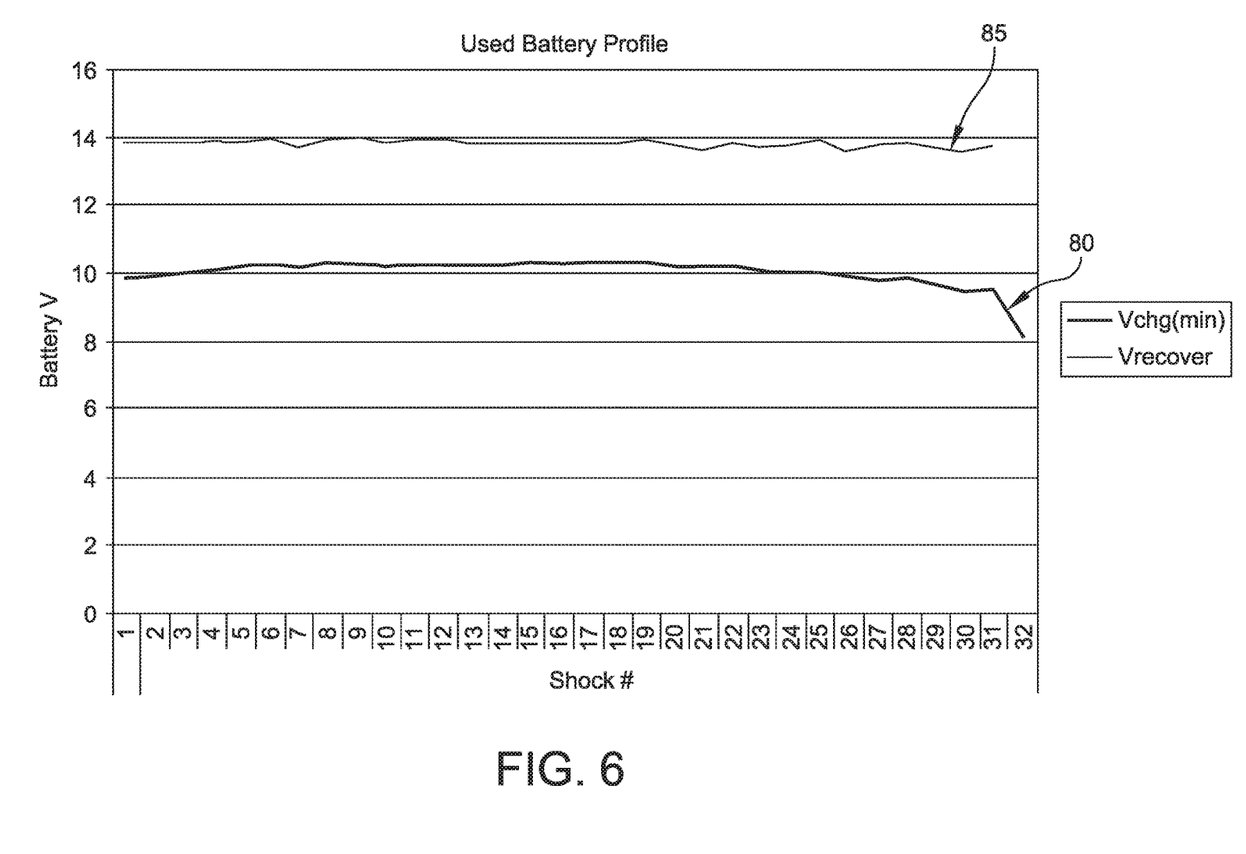
FIG. 6 is a profile of a used battery pack run in the defibrillator for a number of continuous shock cycles, wherein two voltages, i.e., the minimum voltage during charging (Vchg(min)) and the recovered voltage in between shocks (Vrecover), are measured.
Figure 7:
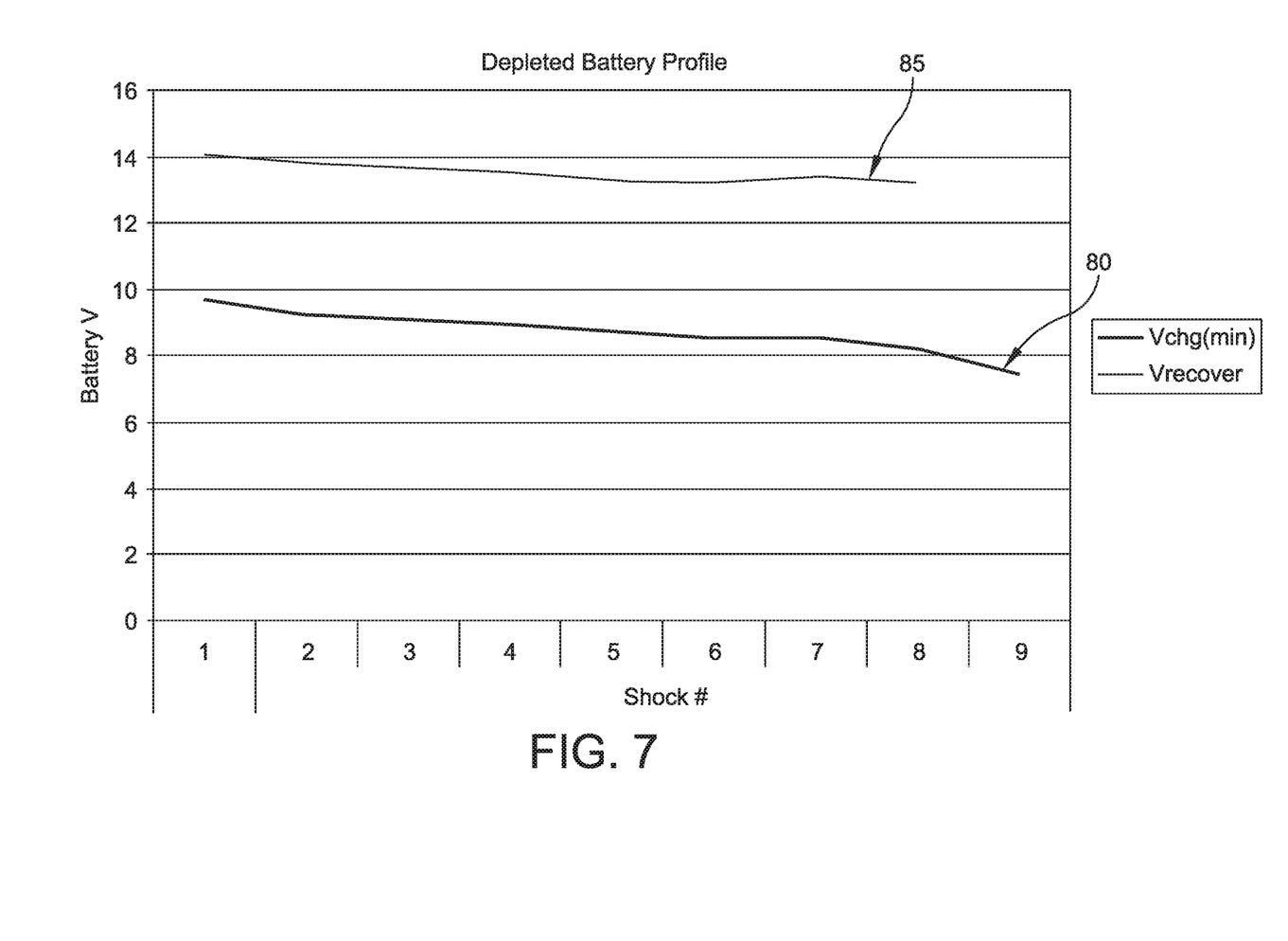
FIG. 7 is a profile of a depleted battery pack run in the defibrillator for a number of continuous shock cycles, wherein two voltages, i.e., the minimum voltage during charging (Vchg(min)) and the recovered voltage in between shocks (Vrecover), are measured.

The varying capacities of battery cells are illustrated in FIGS. 5-7.

FIG. 5 is the profile of a new battery pack measured while the defibrillator is running in AED mode for a number of continuous shock cycles. AED mode is defined as three shocks per minute followed by one minute of rest. The battery profile in FIG. 5 shows two voltage measurements. The first measured voltage, Vchg(min) 80, is the minimum voltage reached during the charge cycle (i.e., while the defibrillator is delivering shocks). The second measured voltage, (Vrecover) 85, is the battery voltage present when the battery has recovered after a charging cycle (i.e., while the battery is "resting" between shocks). As can be seen in the profile of FIG. 5, the measured Vchg(min) 80 is relatively flat with a slight increase in voltage over the first thirty shocks, followed by a slight decrease in approximately the last twelve shocks before the voltage decreases sharply after the last shock (approximately shock number 43 in FIG. 5). This decrease is due to a rise in cell temperature as the defibrillator is delivering shocks. However, the measured Vrecover 85 shows little indication that the battery is depleting at any point measured.

FIG. 6 shows the profile of a used battery pack, also measured while the battery pack is run in a defibrillator for a number of continuous shock cycles. As can be seen, the two voltages measured (Vchg(min) 80 and Vrecover 85) exhibit characteristics similar to that of a new battery, with the exception that Vchg(min) 80 has a lower baseline voltage and the used battery pack has a smaller shock capacity than the new battery pack.

FIG. 7 shows the profile of a depleted battery pack. While the depleted battery pack is capable of delivering several shocks, both voltages (Vchg(min) 80 and Vrecover 85) are gradually decreasing. The depleted battery pack has a much lower shock capacity than both the new and used battery packs (FIGS. 5 and 6, respectively) it should be appreciated that the depleted battery in this case should not be confused with a deeply discharged battery. A deeply discharged battery is unable to sustain a voltage even under a nominal load.

As can be seen in FIG. 7, a depleted battery pack, does not provide the defibrillator with a reliable source of power. Yet, it is critical in life saving situations that the device reliably notify the user that the battery is low. Many current AED units use a battery monitoring circuit, also known as a "smart battery", to provide a "fuel gauge" for remaining battery capacity. This technique requires the use of low power analog and digital circuitry within the battery pack, or within the device, to constantly monitor battery capacity. Many current devices also monitor battery cell temperature to accurately gauge capacity. The disadvantage of this technique is that the additional circuitry, components and connections which are needed for battery monitoring add significant cost to the battery pack and/or the AED unit itself. Therefore, this "fuel gauge" technique has been historically problematic and has been an issue with portable AEDs with both disposable and rechargeable battery packs.

To overcome these issues, the AED of the present invention uses a data acquisition system that measures the current battery voltage and stores the data, along with historical information, for analysis, thereby eliminating the need for using additional circuitry, components and connections.

Looking again at FIGS. 1 and 2, there is shown the battery pack 5 of the defibrillator 15. Battery pack 5 preferably comprises Lithium Manganese Dioxide type cells, however, the method and apparatus of the present invention may be applied to other cell chemistries as well including, but not limited to, Alkaline Manganese Dioxide or rechargeable types, Nickel-Metal Hydride types or Lithium Ion types, etc. A preferred embodiment of the battery pack uses five battery cells, however, the battery pack may easily implement a different number of battery cells. The voltage of each of the five single battery cells is 3V, therefore, the defibrillator supply voltage is 15V. The present invention could also be utilized with more or less battery cells and/or other supply voltages.

Battery pack 5, preferably placed in a plastic housing, is inserted into defibrillator 15 as shown in FIG. 2.

Figure 3:
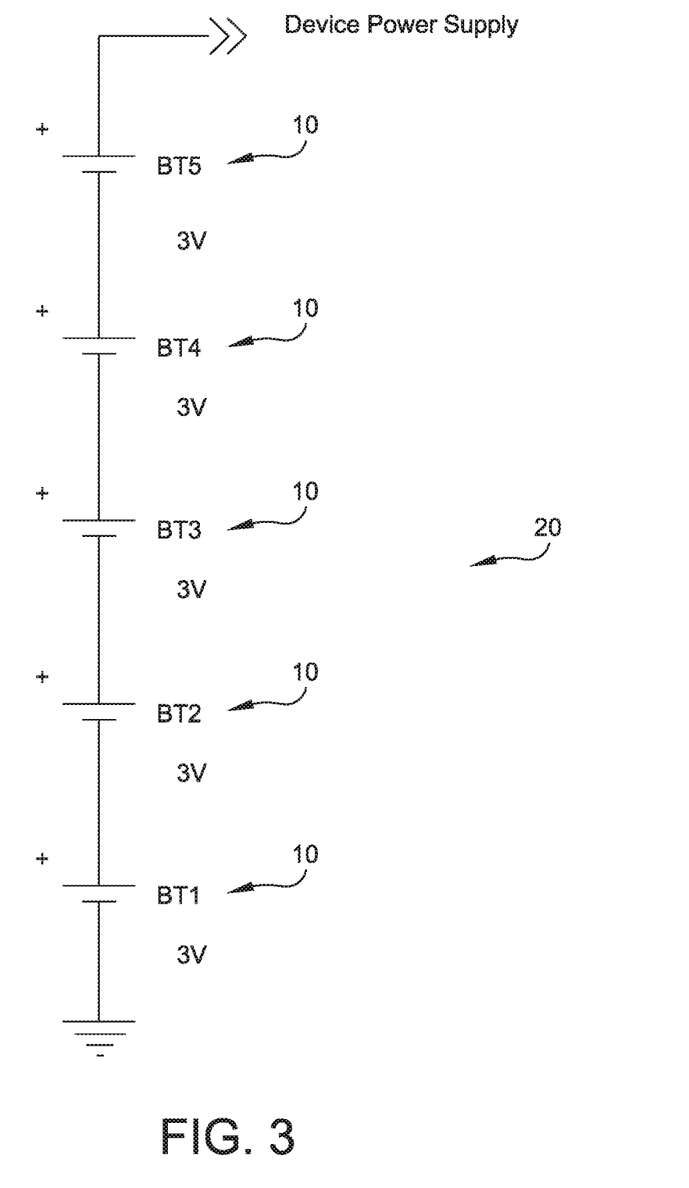
FIG. 3 is a schematic drawing showing the cell arrangement of the battery pack.

A schematic of the five-cell arrangement 20, comprising five individual cells 10, each with a supply voltage of 3V, is shown in FIG. 3.

Figure 4:
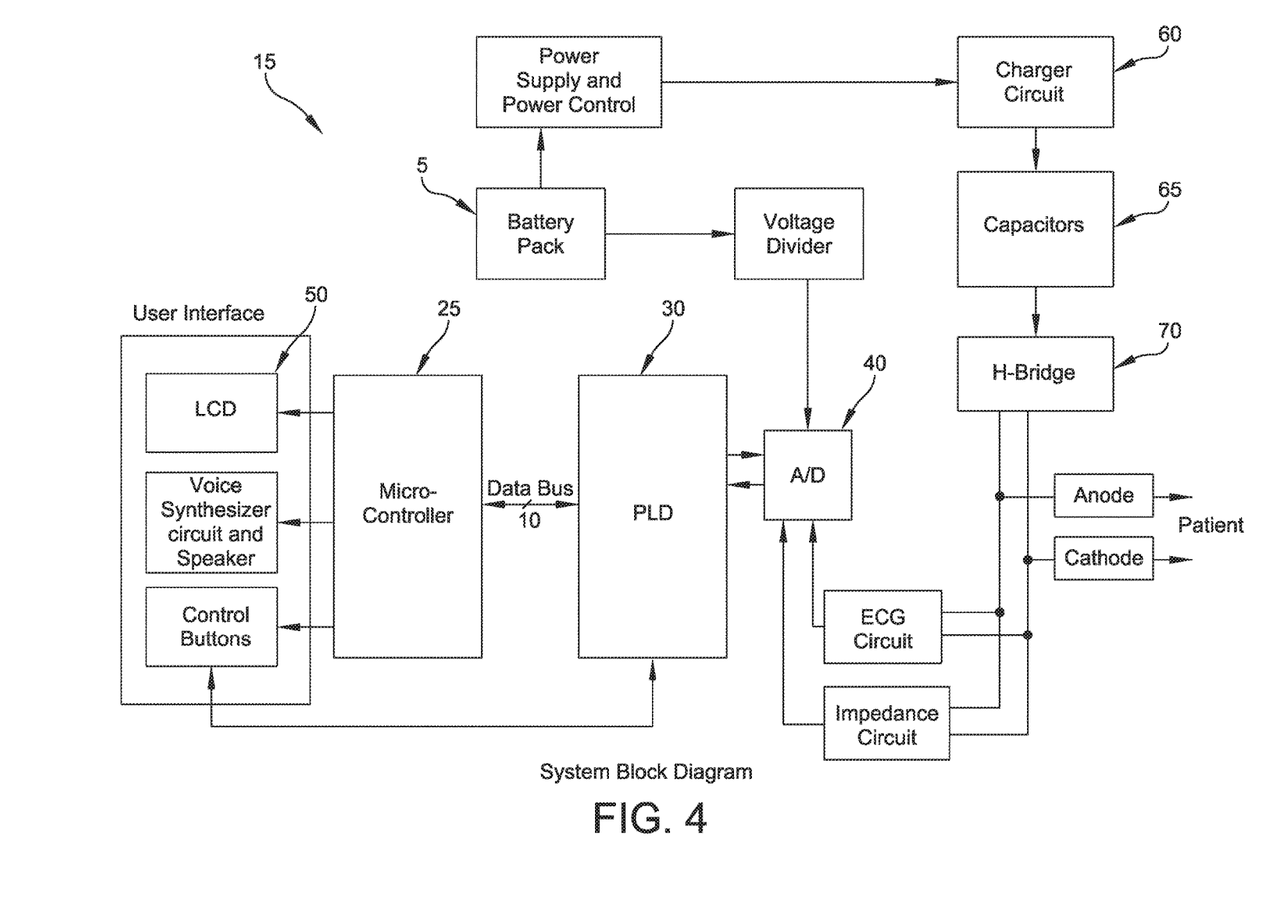
FIG. 4 is block diagram of the defibrillator components.

A block diagram of the defibrillator components is shown in FIG. 4. Defibrillator 15 contains a data acquisition system including, but not limited to, microprocessor 25, programmable logic device (PLD) 30, memory (not shown) and analog-to-digital converter 40.

The preferred embodiment of the invention uses microprocessor 25 to execute instructions to (i) sample data, (ii) store the data into memory, and (iii) process the data to determine the remaining battery capacity. In a preferred embodiment, programmable logic device 30 controls the interface to analog-to-digital converter 40 and stores the sampled data into a local memory buffer. Programmable logic device 30 then interrupts microprocessor 25 to sample the data contained in the buffer, via data-bus 45 connected between microprocessor 25 and PLD 30. Microprocessor 25 may also directly interface to analog-to-digital converter 40 and use internal timing to interrupt microprocessor 25 for sampling frequency. Additionally, microprocessor 25 may be a microcontroller and have memory, analog-to-digital converter 40 and other peripherals on a single chip.

The defibrillator also contains LCD screen 50, as well as a voice synthesizer and speaker for instructing the rescuer. Defibrillator 15 also contains all the necessary components for defibrillation including, but not limited to, charger circuit 60, battery pack 10, capacitors 65 and an H-bridge circuit 70.

The defibrillator data acquisition system samples the battery voltage once every 45 mS (22.22 Hz) and stores the data into random access memory (RAM). The data acquisition system may also store the battery data onto a removable multi-media flash card for post-incident review. Defibrillator 15 is also capable of storing the battery data into EEPROM, Flash or other types of memory well known in the art.

Defibrillator 15 does not need to implement a digital filter, however, a digital filter, such as, but not limited to, an averaging filter (smoothing filter), low-pass filter or other filters well known in the art, may easily be implemented.

Defibrillator 15 may also store historical information into RAM. Such data may contain information about the period of time since the device was last used, the number of times the device has been used, the operational mode of the device and the number of shocks that have been delivered. The device may additionally store its historical information onto a removable multi-media flash card for post-incident review. Defibrillator 15 is also capable of storing its historical information into EEPROM, Flash or other types of memory well known in the art.

Figure 8:
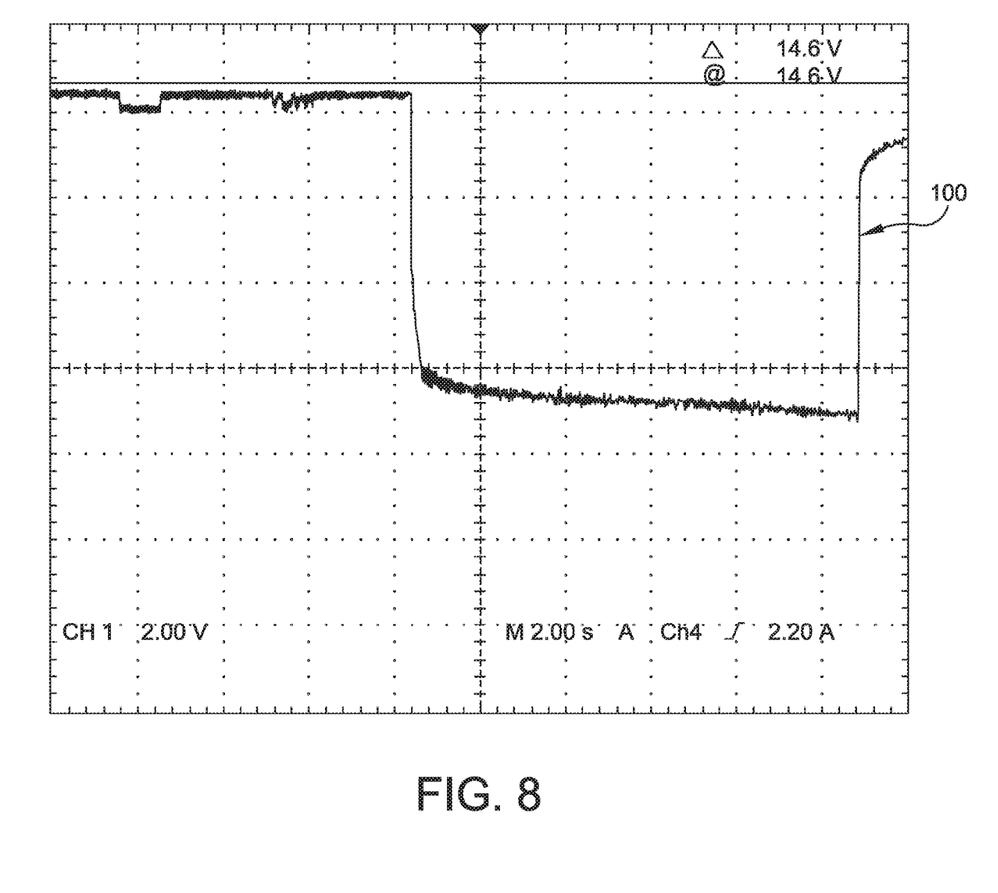
FIG. 8 is an oscilloscope display showing the battery voltage drop during a defibrillator charge cycle.

In one embodiment of the present invention, the method for determining the remaining battery capacity of defibrillator 15 may apply an algorithm that uses battery voltage values in conjunction with the device's historical information. Different thresholds for different modes of the defibrillator operation may be used when applying the algorithm to determine the remaining battery capacity of defibrillator 15. As shown in FIG. 8, for example, voltage 100 drops significantly when the defibrillator begins to charge. The method of the present invention uses a predetermined threshold for when the defibrillator is in idle mode (monitor mode) and applies an algorithm using multiple thresholds for when the defibrillator is in charge mode (charging the capacitors in preparation to provide a shock). The algorithm takes into account, among other things, how long it has been since the defibrillator was last used, how many times the capacitors have been charged and how many times the defibrillator has delivered a shock.

Figure 9:
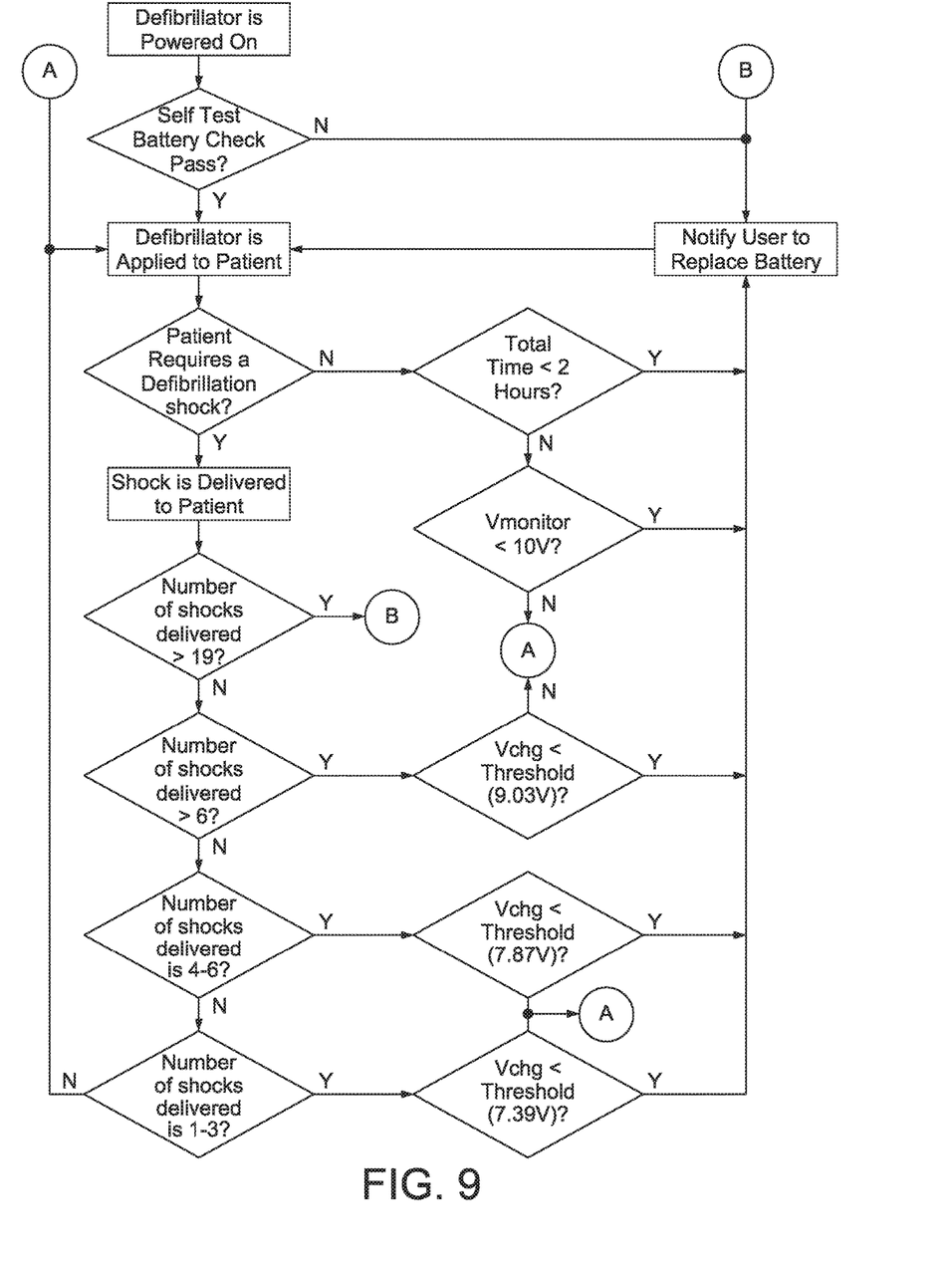
FIG. 9 is a flow diagram showing a preferred algorithm for determining battery capacity.

As shown in the flow diagram of FIG. 9, the defibrillator uses three predetermined thresholds based, on the number of shocks delivered, to determine the charge remaining in the battery pack. The method of the present invention preferably uses a threshold of 7.39 volts for one to three shocks, a threshold of 7.87 volts for three to six shocks, and a threshold of 9.03 volts for more than six shocks. When in idle (i.e., monitoring) mode, the method of the present invention uses a single threshold of 10 volts. When the defibrillator battery cell's voltage falls below the predetermined threshold, the algorithm will determine that a battery capacity remaining is capable of, for example, a minimum of six shocks, although in some cases may be able to deliver up to a maximum of twelve shocks. The rescuer is notified to replace the battery by means of visual and audible messages.

It should be appreciated that the method for determining the remaining battery capacity of defibrillator 15 uses delays between modes to allow the battery voltage to recover. As can be seen in FIG. 8, it can take several hundred milliseconds for the battery to recover after charge mode.

The algorithm used in the method for determining remaining battery capacity also takes into account the total number of shocks delivered. When the device has reached a predetermined threshold for the number of shocks delivered, the device proceeds to notify the user to replace the battery. In one embodiment of the present invention, the defibrillator may use a twenty-shock count threshold.

In addition, the algorithm used in the method of the present invention for determining remaining battery capacity also takes into account the total time the device has been used. When the device has reached a predetermined threshold for the total time of use, the device proceeds to notify the user to replace the battery. In one embodiment of the present invention, the defibrillator may use a two-hour time threshold.

Modifications

It is to be understood that the present invention is by no means limited to the particular constructions herein disclosed and/or shown in the drawings, but also comprises any modifications or equivalents within the scope of the invention.

What is claimed is:

1. A method for notifying a user to replace a battery in a defibrillator, the method comprising:
   measuring the battery voltage during operation of the defibrillator;
   counting the number of shocks delivered during operation of the defibrillator; and
   notifying the user that the battery in the defibrillator needs to be replaced when:
   (i) the number of shocks delivered during operation of the defibrillator is >19; or
   (ii) the number of shocks delivered during operation of the defibrillator is >6 and the battery voltage measured during operation of the defibrillator is <9.03 volts; or
   (iii) the number of shocks delivered during operation of the defibrillator is between 6 and 4, and the battery voltage measured during operation of the defibrillator is <7.87 volts; or
   (iv) the number of shocks delivered is between 3 and 1, and the battery voltage measured during operation of the defibrillator is <7.39.

2. A method according to claim 1 wherein the battery voltage is measured once every 45 mS during operation of the defibrillator.

* * * * *